United States Patent [19]

Eguchi et al.

[11] 4,387,232

[45] Jun. 7, 1983

[54] PROCESS FOR PREPARING N-ACYLCARNOSINE

[75] Inventors: Chikahiko Eguchi, Yokohama; Fusayoshi Kakizaki; Hirozumi Eto, both of Kawasaki, all of Japan

[73] Assignee: Ajinomoto Company Incorporated, Tokyo, Japan

[21] Appl. No.: 329,071

[22] Filed: Dec. 9, 1981

[30] Foreign Application Priority Data

Dec. 18, 1980 [JP] Japan ................................ 55-179287

[51] Int. Cl.$^3$ ............................................ C07D 233/64
[52] U.S. Cl. .................................................... 548/344
[58] Field of Search ........................................ 548/344

[56] References Cited

PUBLICATIONS

March, J. *Advanced Organic Chemistry*, McGraw Hill, New York, 1968, pp. 335, 336 and 339.
Lukton, A., et al., *J. Org. Chem.*, 26, 617, (1961), [C.A. 55, 16520a, (1961)].

*Primary Examiner*—Richard A. Schwartz
*Attorney, Agent, or Firm*—Oblon, Fisher, Spivak, McClelland & Maier

[57] ABSTRACT

A new process is disclosed for preparing N-acylcarnosine which comprises reacting histidine with 3-acylaminopropionic acid reactive derivatives under basic conditions, and 3-acylaminopropionic acid reactive derivative being acid chloride, mixed acid anhydride salt with sulfuric acid, mixed acid anhydride with mono alkyl carbonate or mixed acid anhydride with phosphoric acid derivatives.

7 Claims, No Drawings

PROCESS FOR PREPARING N-ACYLCARNOSINE

The present invention relates to a new process for preparing N-acylcarnosine.

N-Acylcarnosine has the structure of N-acyl-$\beta$-alanylhistidine and particularly N-acetyl-$\beta$-alanyl-L-histidine is useful as medicine owing to its strong controlling action to the cerebrum surroundings. Also, its aluminum salt are useful for preventing or healing ulcers of the digestive tract.

The following processes have been proposed to prepare N-acylcarnosine: (1) A. Lukton and A. Sisti reported in J. Org. Chem., 26, 617(1961) a process for preparing N-acylcarnosine by acetylation of L-carnosine with acetic anhydride. (2) G. Bailin and A. Lukton, J. Org. Chem., 27, 684(1962) discloses that N-acylcarnosine may be prepared by a process which comprises condensing 3-acylaminopropionic acid wherein acyl radical is acetyl or benzoyl radical with p-nitrophenol in the presence of N,N-dicyclohexylcarbodiimide to form p-nitrophenol ester of 3-acylaminopropionic acid, which is in turn condensed with histidine methyl ester to prepare N-acylcarnosine methyl ester, which is in turn hydrolyzed with base to N-acylcarnosine. (3) Japanese Patent Publication No. 14741/1966 discloses a process for preparing N-acetylcarnosine which comprises condensing 3-acetylaminopropionic acid with histidine methyl ester in the presence of N,N-dicyclohexylcarbodiimide to form N-acylcarnosine methyl ester and hydrolyzing the methyl ester with alcoholic potassium hydroxide. However, each of these known processes is not suitable for commercial production of N-acylcarnosine from the following reasons. In case of the prior art (1) process, racemization of the raw material L-carnosine occurs during acetylation and the nitrogen atom in the histidine nucleus is acetylated at the same time whereupon undesirable by-product is formed. In case of the prior art (2) and (3) processes, N,N-dicyclohexylcarbodiimide to be employed as condensing agent is expensive and causes safety problem owing to its irritative property to the mucous membrane of eyes. And the processes include many steps because of use of histidine methyl ester.

An object of the present invention is to provide a new process for preparing N-acylcarnosine from histidine and 3-acylaminopropionic acid reactive derivatives which possesses advantages over the known processes. The present process avoids the use of expensive N,N-dicyclohexylcarbodiimide. In particularly it provides a process involving fewer steps than the known processes and enables the N-acylcarnosine to be prepared in high yield in a manner extremely suitable for commercial production.

According to the present invention, there is provided a process for preparing N-acylcarnosine having the general formula

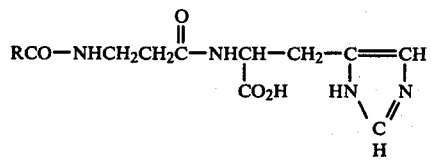

wherein RCO is aliphatic acyl or aromatic acyl radical which comprises reacting histidine with a 3-acylaminopropionic acid reactive derivative having the general formula

wherein R is as defined above, and X is —Cl, —OSO$_3^\ominus$Y$^\oplus$ wherein Y$^\oplus$ is tertiary organic amine cation or alkali metal cation, —OPOCl$_2$ or

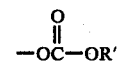

wherein R' is alkyl radical, under basic condition.

The present process may be represented by the following reaction scheme wherein the symbols are as hereinbefore defined.

(I)

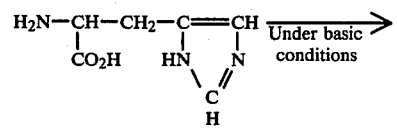

(II)

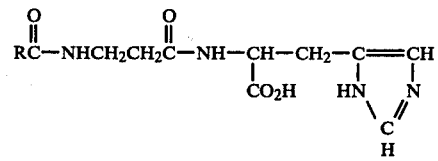

(III)

The 3-acylaminopropionic acid reactive derivatives to be reacted with histidine in the present process may be easily prepared by reacting 3-acylaminopropionic acid with the corresponding acid activating agent in an organic solvent such as methylene chloride, ethylene dichloride, dioxane, tetrahydrofuran, ethyl acetate or methyl isobutyl ketone.

3-Acylaminopropionyl chloride which X in the general formula (I) is chlorine (Cl) may be easily prepared by reacting 3-acylaminopropionic acid with thionyl chloride in methylene chloride at room temperature, as disclosed in U.S. Pat. No. 3,749,712. Mixed acid anhydride tertiary amine salt of 3-acylaminopropionic acid and sulfuric acid which X is —OSO$_3^\ominus$Y$^\oplus$ wherein Y$^\oplus$ is tertiary amine cation may be prepared by reacting 3-acylaminopropionic acid with sulfuric anhydride or chlorosulfonic acid in the presence of tertiary amine such as trimethylamine, triethylamine, tri-n-butylamine, N-methylmorpholine and the like at a temperature of 5°–35° C. Alternatively, mixed acid anhydride alkali metal salt such as lithium salt of 3-acylaminopropionic acid and sulfuric acid wherein X is —OSO$_3^\ominus$Y$^\oplus$ wherein Y$^\oplus$ is alkali metal cation may be prepared by reacting alkali metal salt of 3-acylaminopropionic acid with sulfuric anhydride. Mixed acid anhydride of 3-acylaminopropionic acid and phosphoric acid derivatives, which X is —OPOCl$_2$, may be prepared by reacting 3-acylaminopropionic acid with phosphorous oxychloride (POCl₃) in the presence of tertiaryamine at a temperature between −20° C. and −5° C. And mixed acid anhydride of 3-acylaminopropionic acid and monoalkylcarbonate, which X is

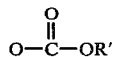

may be prepared by reacting 3-acylaminopropionic acid with chloroformic acid ester in the presence of tertiary amine at a temperature between −15° C. and 0° C. Ester moiety in the chloroformic acid ester may be $C_1$–$C_5$ alkyl ester such as methyl, ethyl, propyl, isopropyl, isobutyl and amyl. In all cases, the reaction is completed within from 10 minutes to 2 hours.

An acyl radical in 3-acylaminopropionic acid reactive derivative which may be employed as the starting material in the present process may be either aliphatic or aromatic acyl radical. Examples of aliphatic acyl radicals are acetyl, propionyl, buthyryl, lauroyl, palmitoyl and stearoyl. And examples of aromatic acyl radical are benzoyl, naphthoyl and phenylacetyl radicals.

Histidine which is an another raw material in the present process may be employed in the form of free one or its hydrochloride. It may be either racemic or optionally active form, but L-form is usually employed.

In carrying out the present process, 3-acylaminopropionic acid reactive derivative is added as it is or in solution dissolved in an organic solvent to solution of histidine in water alone or in a mixed solvent of water and water miscible organic solvent, under basic condention. As water miscible solvents, for example acetone, acetonitrile and methanol may be employed. As organic solvent, there may be employed acetone, acetonitrile, chloroform, dichloromethane, ethylene dichloride, methyl isobutyl ketone and the like. As basic condition, the pH of the reaction medium is maintained to 9.0–12, preferably 9.5–10.5 with inorganic bases such as sodium hydroxide and potassium hydroxide or organic bases such as triethylamine and pyridine whereby undesirable side reaction may be depressed extremely to give high yield of the desired N-acylcarnosine.

For the purpose of maintaining the pH to the above range during the cource of reaction, 3-acylaminopropionic acid reactive derivative and a solution of base is slowly added simultaneously to the solution of histidine.

The reaction temperature may be below 30° C. preferably 5 to 10° C. There is no danger of racemization even when optically active histidine is employed.

Histidine is generally more expensive than 3-acylaminopropionic acid reactive derivative and hence the latter is employed in excess, preferably in 1.5 to 2.5 times mole.

After the reaction has been completed, the isolation and purification of the desired N-acylcarnosine from the reaction mixture may be conveniently conducted by the following manner. The reaction mixture is treated with strongly acidic ion exchange resins (H form) such as "Diaion SK-1B" (trade name), "Amberlite IR-120" (trade name) and "Dowex 50W" to adsorb N-acylcarnosine thereon, whereby N-acylcarnosine may be efficiently separated from 3-acylaminopropionic acid which is derived from the hydrolysis of 3-acylaminopropionic acid reactive derivative, and inorganic materials. Thereafter, the adsorbed N-acylcarnosine on the resin is eluted with an aqueous ammonia. The eluate is concentrated under reduced pressure to remove ammonia and further treated with weakly acidic ion exchange resin (H form) such as "Amberlite IRC-50" (trade name) to remove the remaining unreacted histidine and ammonia whereby highly purified N-acylcarnosine is obtained.

The present invention is further illustrated by the following examples.

EXAMPLE 1

31.0 Grams of L-histidine was dissolved in 400 ml of water and the solution was adjusted to pH 9.8 with about 50 ml of 2 N aqueous sodium hydroxide solution. To the solution under stirring, were simultaneously added dropwise a solution of 59.6 g of 3-acetylaminopropionyl chloride (acid chloride of N-acetyl-β-alanine) in 100 ml of chloroform and about 500 ml of 2 N aqueous sodium hydroxide solution, while the reaction system was maintained to a pH ranging from 9.5 to 10.0 and to a temperature ranging from 5° to 10° C. After addition, stirring was continued for 1 hour at that temperature.

The reaction solution was settled and chloroform layer was separated out. The aqueous layer was passed through a column of 1.0 l of strongly acidic ion exchange resin "Diaion SK-1B" (H form) to adsorb the formed N-acetyl-L-carnosine thereon.

Thereafter, the column was washed with water until the washing became neutral. And 1.5 l of 1.5 N aqueous ammonia solution was passed through the column to elute N-acyl-L-carnosine and the column was washed with 2.5 l of water. The eluate and washings were combined and concentrated under reduced pressure to a volume of 700 ml. The concentrate was passed through a column of 200 ml of weakly acidic ion exchange resin "Amberlite IRC-50" (H form) and the column was washed with water until washing became neutral. The combined effluent and washings was concentrated under reduced pressure to a volume of 75 ml. This concentrate was warmed to 50° C. and 350 ml of isopropyl alcohol was slowly added. The mixed solution was allowed to stand overnight at room temperature. The precipitated crystals were filtered out and dried. There was obtained 34.5 g of crude crystals of N-acetyl-L-carnosine.

34.5 Grams of the crude crystals were dissolved in 200 ml of water and the solution was treated with 5.0 g of active charcoal. The active charcoal was filtered off and washed with 50 ml of water. The filtrate and washing were combined and concentrated under reduced pressure to a volume of 70 ml. The concentrate was warmed to 60° C. and 300 ml of isopropyl alcohol was added thereto and the mixed solution was allowed to stand overnight at room temperature. The precipitated crystals were filtered out and dried to yield 31.0 g of the purified N-acetyl-L-carnosine.

The crystals were negative to ninhydrin reaction, soluble in water and insoluble in acetone, ethyl ether and petroleum ether.

| Specific rotation power: $[\alpha]_D^{20} = +26.5$ (C = 3, $H_2O$) | | | |
|---|---|---|---|
| Analysis | | | |
| | C | H | N (%) |
| Calculated for $C_{11}H_{16}O_4N_4$ | 49.25 | 6.01 | 20.88 |
| Found | 49.13 | 6.20 | 20.75 |

The infrared absorption spectrum (IR) and high resolution nuclear magnetic resonance absorption spectrum (NMR) were identical with those of an authentic sample of N-acetyl-L-carnosine.

EXAMPLE 2

3.10 Grams of L-histidine was suspended in a mixed solvent of 40 ml of acetone and 40 ml of water, and then 5 ml of 2 N-aqueous sodium hydroxide solution was added, whereby a solution of pH 9.5 was prepared. To this solution under stirring, were simultaneously added dropwise a solution of 5.98 g of 3-acetyl-aminopropionyl chloride in 10 ml acetone and 43 ml of 2 N-aqueous sodium hydroxide solution, while the reaction system was maintained to a temperature below 10° C. and to a pH ranging from 9.0 to 10.0. After stirring for additional 30 minutes at room temperature, acetone was distilled off under reduced pressure. The concentrate was mixed with 50 ml of water and treated with strongly acidic ion exchange resin and weakly acidic ion exchange resin by similar procedure as in Example 1. Crystallization from water-isopropyl alcohol was twice conducted to yield 2.9 g of the purified crystals of N-acetyl-L-carnosine.

The specific rotation power, IR and NMR were identical with those of an authentic sample.

EXAMPLE 3

3.1 Grams of histidine was suspended in mixed solvent of 40 ml of water and 40 ml of acetone. To the suspension was added about 5 ml of 2 N aqueous sodium hydroxide solution whereby a solution of pH 9.8 was prepared. To the solution under stirring, were simultaneously added dropwise a solution of 8.4 g of 3-benzoylaminopropionyl chloride in 15 ml of acetone and about 20 ml of 2 N aqueous sodium hydroxide solution while the reaction system was maintained to a temperature below 10° C. and a pH range of 9.5-10.0. After stirring for additional 30 minutes at room temperature, acetone was distilled off under reduced pressure and the concentrate was mixed with 50 ml of water and then treated with strongly acidic ion exchange resin and weakly acidic ion exchange resin according to Example 1. Crystallization from water-isopropyl alcohol mixed solvent was conducted to yield 3.4 g of the purified crystals of N-benzoyl-L-carnosine. M.P. 215°-218° C.

The specific rotation, IR and NMR were identical with those of an authentic sample.

EXAMPLE 4

52.4 Grams of 3-acetylaminopropionic acid was dissolved in a mixed solvent of 40 ml of methylene chloride and 40.4 g of triethylamine. To the resultant solution which was stirred keeping the temperature below 10° C., was added dropwise 70 ml of methylene chloride solution containing 32 g of sulfuric anhydride. The mixed solution was stirred for 10 minutes at room temperature to prepare the methylene chloride solution containing 124.8 g of triethylamine salt of 3-acetylaminopropionic acid and sulfuric acid mixed acid anhydride.

On the other hand, 400 ml of water was added to 31.0 g of histidine and then adjusted to pH 10.5 with about 50 ml of 2 N aqueous sodium hydroxide solution. To this solution were simultaneously added dropwise 220 ml of methylene chloride containing 124.8 of triethylamine salt of 3-acetylaminopropionic acid sulfuric acid mixed acid anhydride prepared previously and 350 ml of 2 N aqueous sodium hydroxide solution while the temperature and pH were kept to 5°-10° C. and 10.3°-10.5° C. respectively.

After stirring for additional 30 minutes at room temperature, the reaction solution was settled. The lower layer (methylene chloride layer) was separated out. The aqueous layer was passed through a column of 1.0 l of strongly acidic ion exchange resin "Diaion SK-1B" (H form) to adsorb the formed N-acetyl-L-carnosine thereon. Thereafter the column was washed with water until the washings became neutral. 1.5 Liter of 1.5 N aqueous ammonia was passed through the column to elute N-acetyl-L-carnosine and the column was washed with 2.5 l of water. The eluate and washing were combined and concentrated to a volume of 700 ml under reduced pressure.

The concentrate was passed through a column of 200 ml of weakly acidic ion exchange resin "Amberlite IRC-50" (H form) and the column was washed with water until washings became neutral. The combined effluent and washings were concentrated to a volume of 75 ml under reduced pressure. This concentrate was warmed to 50° C. and 430 ml of isopropyl alcohol was slowly added thereto and was allowed to stand overnight at room temperature. The precipitated crystals were filtered out and dried to yield 42.3 g of crude N-acetyl-L-carnosine crystals. 42.3 Grams of the crude crystals was dissolved in 240 ml of water and treated with 6.0 g of active charcoal for decolorization. The active charcoal was filtered off and washed with water. The decolorized solution and washing were combined together and concentrated to a volume of 70 ml under reduced pressure. This concentrate was warmed to 60° C. and 360 ml of isopropyl alcohol was added thereto. After standing overnight at room temperature, the precipitated crystals were filtered out and dried to yield 38.0 g of the purified N-acetyl-L-carnosine crystals.

This substance was negative to ninhydrin reaction and soluble in water, and insoluble in acetone, ethyl ether and petroleum ether. It had a specific rotation power of $[\alpha]_D^{20} = +26.6$ (C=3, H$_2$O). The infrared spectrum (IR) and high resolution nuclear magnetic resonance (NMR) were identical with those of an authentic sample of N-acetyl-L-carnosine.

EXAMPLE 5

5.24 Grams of 3-acetylaminopropionic acid was dissolved in a mixed solvent of 25 ml of chloroform and 4.04 g of triethylamine. To the solution which was stirred keeping the temperature below −5° C., was added 6.83 g of isobutyl chloroformate. After stirring for additional 20 minutes at room temperature, the resultant solution and 20 ml of 2 N aqueous sodium hydroxide solution were simultaneously added dropwise to 45 ml of aqueous solution containing 3.10 g of histidine which has been adjusted to a pH of 10.50 while the reaction system was stirred and maintained to a temperature below 10° C. and a pH between 10.30 and 10.50. After stirring for additional 30 minutes at room temperature, the reaction solution was settled and the lower layer (chloroform layer) was separated out. The aqueous layer was treated by a similar manner as in Example 4 to obtain 3.65 g of N-acetyl-L-carnosine crystals. The specific rotation power $[\alpha]_D^{20}$ was 26.5 (C=3, H$_2$O). Also, the infrared spectrum (IR) and high resolution nuclear magnetic resonance (NMR) were identical with those of an authentic sample.

EXAMPLE 6

25 Ml of chloroform and 4.04 g of triethylamine were added to 7.46 g of 3-benzoylaminopropionic acid, which was dissolved therein. The solution was stirred at a temperature below −5° C. and 5.78 g of isobutyl chloroformate was added dropwise thereto. After stirring for 20 minutrs at room temperature, the resultant solution and 20 ml of 2 N aqueous sodium hydroxide solution were simultaneously added dropwise to 45 ml of aqueous solution containing 3.10 g of histidine which has been adjusted to pH 10.5 while the reaction system was stirred and maintained to a temperature below 10° C. and a pH range between 10.3 and 10.5. After stirring for additional 30 minutes at room temperature, the reaction solution was settled and the chloroform layer was separated out. The aqueous layer was treated by a similar manner as in Example 4 to obtain 5.0 g of N-benzoyl-L-carnosine crystals which had melting point of 215° C.-218° C.

The specific rotation power, IR and NMR were identical with those of an authentic sample.

EXAMPLE 7

49.1 Grams of 3-acetylaminopropionic acid and 73.0 g of tri-n-butylamine were dissolved in 68 ml of methyl isobutyl ketone. To the resultant solution which was stirred keeping the temperature to 5°–10° C., was added a solution of 45.7 g of chlorosulfonic acid and 72.9 g of tri-n-butylamine in 200 ml of methyl isobutyl ketone. After addition, the stirring was continued for 4 hours at room temperature to prepare 370 ml of methyl isobutyl ketone solution containing 148.6 g of tri-n-butylamine salt of 3-acetylaminopropionic acid and sulfuric acid mixed acid anhydride.

On the other hand, 52.4 g of L-histidine hydrochloride monohydrate was dissolved in 400 ml of water and the solution was adjusted to pH 10.5 with about 112 ml of 4 N aqueous sodium hydroxide solution. To this solution were simultaneously added dropwise 370 ml of methyl isobutyl ketone solution containing 148.6 g of tri-n-butylamine salt of 3-acetylaminopropionic acid-sulfuric acid mixed acid anhydride which has been prepared previously and 330 ml of 4 N aqueous sodium hydroxide solution while the reaction medium was stirred and maintained to a pH of 10.3–10.5 and a temperature of 5°–10° C. After stirring for 30 minutes at room temperature, the reaction was adjusted to pH 13.0 with about 300 ml of 4 N aqueous sodium hydroxide solution and allowed to stand. The upper methyl isobutyl ketone layer was separated out and the lower aqueous layer was treated by a similar manner as in Example 4 to obtain 49.6 g of N-acetyl-L-carnosine crystals.

The specific rotation power $[\alpha]_D^{20} = 26.8$ (C=3, H$_2$O). The IR and NMR were identical with those of an authentic sample.

EXAMPLE 8

5.24 Grams of 3-acetylaminopropionic acid was dissolved in a mixed solvent of 30 ml of ethylene dichloride and 7.41 g of tri-n-butylamine, and then 3.08 g of phosphorous oxychloride was added dropwise thereto while stirring was operated and the temperature was maintained to below 10° C. After addition, the stirring was continued for 10 minutes at room temperature.

The resultant solution and 42 ml of 4 N aqueous sodium hydroxide solution were simultaneously added dropwise to 45 ml of aqueous solution containing 3.10 g of histidine which was adjusted to pH 10.00 while the reaction system was stirred and maintained to a pH of 9.8–10.0 and a temperature below 10° C. After stirring for additional 30 minutes at room temperature, the reaction solution was adjusted to pH 13.0 with 42 ml of 4 N aqueous sodium hydroxide solution and then settled to form two layers. The layer ethylene dichloride layer was separated out and the upper aqueous layer was treated by a similar manner as in Example 4 to obtain 2.70 g of N-acetyl-L-carnosine crystals. The specific rotation power IR and NMR were identical with those of an anthentic sample.

What we claim is:

1. A process for preparing N-acetyl-L-carnosine which comprises reacting L-histidine with a 3-acetylaminopropionic acid reactive derivative at a pH range between 9.0 and 12.0 at a temperature below 30° C., said 3-acetylaminopropionic acid reactive derivative being 3-acetylaminopropionic chloride, tertiary amine salt of 3-acetylaminopropionic acid and sulfuric acid mixed anhydride, mixed acid anhydride of 3-acetylaminopropionic acid and monoalkyl carbonate wherein the alkyl radical has 1 to 5 carbon atoms, or mixed acid anhydride of 3-acetylaminopropionic acid and phosphoric acid derivative.

2. A process according to claim 1, wherein 3-acylaminopropionic acid reactive derivative is 3-acetylaminopropionyl chloride.

3. A process according to claim 1, wherein 3-acylaminopropionic acid reactive derivative is tertiary amine salt of 3-acetylaminopropionic acid and sulfuric acid mixed acid anhydride.

4. A process according to claim 1, wherein 3-acylaminopropionic acid reactive derivative is a mixed acid anhydride of 3-acetylaminopropionic acid and monoalkyl carbonate.

5. A process according to claim 1, wherein 3-acylaminopropionic acid reactive derivative is a mixed acid anhydride of 3-acetylaminopropionic acid and phosphoric acid derivatives.

6. A process for preparing N-acetyl-L-carnosine which comprises reacting 3-acetylaminopropionic acid with an acid activating agent selected from the group consisting of thionyl chloride, sulfuric anhydride, chlorosulfonic acid, phosphorous oxychloride and chloroformic acid ester in an organic solvent in the presence of tertiary amine to form the corresponding 3-acetylaminopropionic acid reactive derivative and reacting said 3-acetylaminopropionic acid reactive derivative with histidine at a pH of 9.0 to 12.0 and at temperature below 30° C.

7. A process according to claim 6, wherein said acid activating agent is selected from the group consisting of sulfuric anhydride and chlorosulfonic acid.

* * * * *